US008394076B2

(12) United States Patent
Latina

(10) Patent No.: US 8,394,076 B2
(45) Date of Patent: Mar. 12, 2013

(54) LASER ASSISTED THERAPEUTIC AGENT DELIVERY INTO A TARGETED TISSUE

(76) Inventor: Mark A. Latina, North Andover, MA (US)

( * ) Notice: Subject to any disclaimer, the term of this patent is extended or adjusted under 35 U.S.C. 154(b) by 295 days.

(21) Appl. No.: 12/436,511

(22) Filed: May 6, 2009

(65) Prior Publication Data
US 2009/0287138 A1 Nov. 19, 2009

Related U.S. Application Data

(60) Provisional application No. 61/053,209, filed on May 14, 2008, provisional application No. 61/201,029, filed on Dec. 5, 2008.

(51) Int. Cl.
*A61M 31/00* (2006.01)
(52) U.S. Cl. .......................................... 604/501; 604/20
(58) Field of Classification Search .................. 604/20, 604/500–522; 606/2–6
See application file for complete search history.

(56) References Cited

U.S. PATENT DOCUMENTS

| | | | |
|---|---|---|---|
| 4,741,612 A | 5/1988 | Birngruber et al. | |
| 5,302,259 A | 4/1994 | Birngruber | |
| 5,549,596 A * | 8/1996 | Latina | 606/4 |
| 6,095,648 A | 8/2000 | Birngruber et al. | |
| 7,115,120 B2 | 10/2006 | Lin | |
| 2007/0072933 A1 * | 3/2007 | Peyman | 514/414 |

OTHER PUBLICATIONS

Roider, Johann et al., "Microphotocoagulation: Selective effects of repetitive short laser pulses," *Proc. Natl. Acad. Sci. USA*, vol. 90:8643-8647 (1996).
Johnson, N.F. et al., "Effect of photocoagulation on the barrier function of the pigment epithelium. II. A study by electron microscopy," *Trans. Ophthalmol. Soc. U.K.*, vol. 97(4):640-651 (1977).
Pollack, A. et al., "Restoration of the outer blood-retinal barrier after krypton laser photocoagulation," *Ophthalmic. Res.*, vol. 25(4):201-209 (1993).
Wallow, Ingolf H., "Repair of the Pigment Epithelial Barrier Following Photocoagulation," *Arch. Ophthalmol.*, vol. 102:126-135 (1984).

* cited by examiner

*Primary Examiner* — Kevin C Sirmons
*Assistant Examiner* — Phillip Gray
(74) *Attorney, Agent, or Firm* — Morse, Barnes-Brown & Pendleton, P.C.; Sean D. Detweiler, Esq.

(57) ABSTRACT

The present invention involves selectively breaking down or altering a blocking tissue by irradiating the blocking tissue with a laser irradiation. Breaking down the blocking tissue allows the delivery of therapeutic agents through the blocking tissue to a target tissue. An area of the blocking tissue is selected for treatment. The selected area is irradiated with a laser to induce an alteration or breakdown of the blocking tissue. Areas not irradiated are not affected. Once the selected area of the blocking tissue is treated, a therapeutic agent can be delivered to the selected area and passed through the altered or broken down blocking tissue to the target tissue. The blocking tissue will then undergo a healing response after a period of time. The present invention may be used to treat the retina or subretinal space of a patient's eye through the blocking tissue of the Retinal Pigment Epithelium (RPE).

19 Claims, 4 Drawing Sheets

LASER ASSISTED THERAPEUTIC AGENT DELIVERY INTO A TARGETED TISSUE

RELATED APPLICATIONS

The present Application claims priority to, and the benefit of, U.S. Provisional Patent Application No. 61/053,209, filed on May 14, 2008, and U.S. Provisional Patent Application No. 61/201,029, filed on Dec. 5, 2008. The contents of these Applications are incorporated herein by reference.

FIELD OF USE

The present Application relates to devices, systems, and methods for the treatment of tissue using lasers. Exemplary embodiments relate to the delivery of a therapeutic agent to a target tissue through a blocking tissue layer. For example, exemplary embodiments may be used to deliver a therapeutic agent to the retina in conjunction with a laser procedure.

BACKGROUND

In treating certain medical conditions, the effective delivery of therapeutic agents to a target tissue may be prohibited by blockage. Certain tissue types with low permeability, or cell types with tight junctions, may impede the delivery of drugs to the target tissue. For example, the treatment of various eye conditions such as macular degeneration, macular edema, and central serous retinopathy often requires delivery of medication to the retina or subretinal space of a patient's eye. However, the Retinal Pigment Epithelium (RPE) of the eye can interfere with such delivery of medication. The RPE is the pigmented cell layer outside the retina and is attached to the underlying choroid and overlying retinal visual cells. The RPE acts as a barrier to the transport of molecules into the retina and subretinal space. The RPE allows small molecules, such as amino acids, to pass therethrough while preventing the passage of larger molecules such as blood borne substances provided by the choroid. Thus, it is difficult to deliver large molecule therapeutic agents intravenously or through the surrounding orbital and ocular tissue to the retina or subretinal space.

SUMMARY

In view of the above, it is beneficial to provide a means of delivering of therapeutic agents through a blocking tissue, such as the RPE, to a target tissue, such as the retinal or subretinal space of a patient's eye. Exemplary embodiments use a laser to break down or otherwise alter the blocking tissue (e.g., the RPE) to enable the passage of a therapeutic agent to the target tissue (e.g., the retina or subretinal space of the patient's eye) without permanently damaging any surrounding tissue structures. After treatment of the blocking tissue by the laser, large molecule therapeutic agents may be passed through the blocking tissue into the target tissue for treatment of a condition. In accordance with one exemplary embodiment, the present invention may be used to treat macular degeneration and other diseases of the retina.

According to one embodiment of the present invention, a method of delivering a therapeutic agent to a target tissue, such as a retina of a patient, is disclosed. The method may include irradiating an area of a blocking tissue, such as an area of a retinal pigment epithelium ("RPE") of a patient's eye, with laser radiation in such a way that induces a breakdown or an alteration of the area in an amount sufficient to enable the therapeutic agent to pass through an opening in the blocking tissue.

The therapeutic agent may then be administered to the patient. In accordance with one embodiment of the present invention, the therapeutic agent may be intravenously administered or delivered by local application/injection or iontophoresis, delivered transsclerally, introduced into the subtenon's space, or introduced through a surrounding orbital tissue. In another embodiment, the therapeutic agent may be a pro-drug and/or may be activated by irradiating the agent with laser radiation. The therapeutic agent administered may have a molecular weight, for example, between about 200 and 156000 daltons. The therapeutic agent may be used, for example, to treat a retinal disorder of the patient, such as macular degeneration, retinitis pigmentosa and diabetic retinopathy. In one embodiment, the therapeutic agent is one of pegaptanib sodium, bevacizumab, VEGF Trap, and ranibizumab.

In accordance with one embodiment of the present invention, the laser radiation has a fluence between about 3 µJoules/cm$^2$ and about 2 Joules/cm$^2$. The laser radiation may be provided by, for example, a q-switched Nd:YAG laser, a Pulsed-Dye laser, a continuous wave argon-ion laser, a flashlamp-pumped dye laser, or a Nd:YLF laser. The laser radiation may be delivered using one or more laser pulses or a series of pulses having a duration of between about 1 ns and about 15 µs.

In accordance with further embodiments of the present invention, a contrast agent is also administered.

BRIEF DESCRIPTION OF THE FIGURES

These and other characteristics will be more fully understood by reference to the following detailed description in conjunction with the attached drawings, in which:

FIG. 4b is a cross-section view of a region of tissue at step 410 in FIG. 4a;

FIG. 4c is a cross-section view of a region of tissue at steps 420-430 in FIG. 4a; and FIG. 4d is a cross-section view of a region of tissue at step 440 in FIG. 4a.

DETAILED DESCRIPTION

Figure 1:
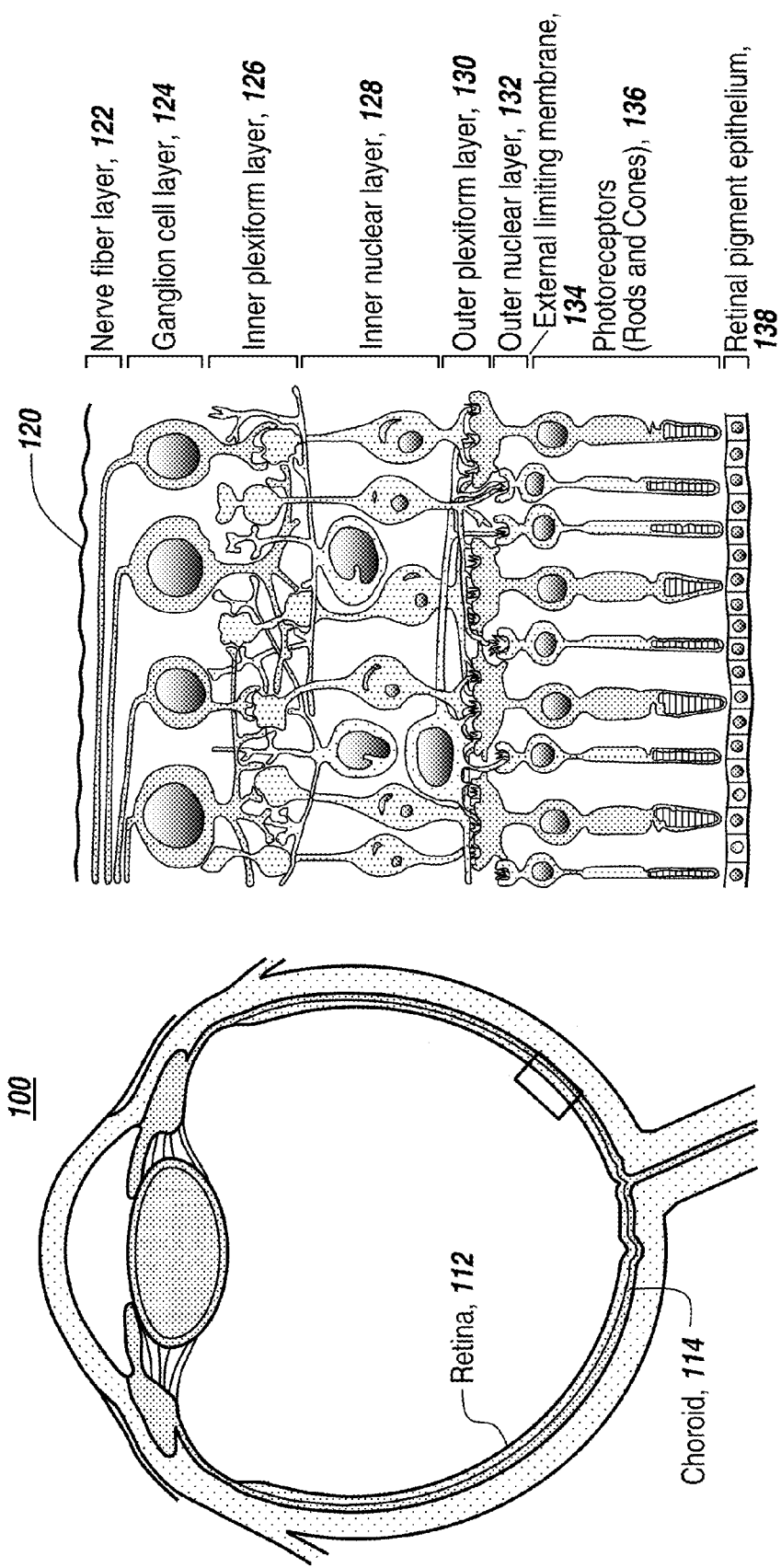
FIG. 1 is a cross-section view 100 of an eye.

Exemplary embodiments selectively break down or alter a blocking tissue layer, for example the Retinal Pigment Epithelium (RPE) of a patient's eye, in order to deliver therapeutic agents through the blocking layer to a targeted tissue, for example the retina or subretinal space of the patient's eye.

Although reference is made to the treatment of eye conditions by delivering therapeutic agents through an RPE blockage layer, one having ordinary skill in the art will recognize that the present invention is not so limited, and may be employed to deliver therapeutic agents through many types of blocking tissues with low permeability, ranging from single layers of cells to bulk tissue.

In one embodiment, an area of the Retinal Pigment Epithelium (RPE) of the patient's eye is selected for treatment. The selected area is irradiated with a laser to induce breakdown or alteration of the RPE. Areas not irradiated may remain unaffected. Once the selected area of the RPE is altered by the laser treatment, a therapeutic agent may be delivered to the selected area either by intravenous administration or by trans-scleral or peri-orbital administration and passed through the altered or targeted broken down RPE to the retinal or subretinal space of the patient's eye. The RPE will then undergo healing after a period of time. Unlike conventional laser therapy of the retina where the RPE and the overlying retina is affected, this technique spares damage to the overlying photoreceptors and overlying retina.

The term "patient" as utilized herein is meant to include any mammal to which ocular laser therapy may be administered. Patients specifically intended for treatment by the methods described herein include humans, as well as non-humans.

The term "treating," or variations thereof, as used herein is intended to encompass curing as well as ameliorating at least one symptom of a condition or disease. In one embodiment, the methods described herein are used to deliver a therapeutic agent for the treatment of a retinal disease, such as, but not limited to, macular degeneration.

Exemplary embodiments may be used to treat retinal disorders. Symptoms of retinal disorders include, but are not limited to, poor vision at night (night blindness) and trouble adjusting from brightly lit areas to dim ones; sudden or unexplained loss of vision; loss of peripheral vision; loss of vision in a particular visual field; nystagmus, a rapid, involuntary oscillatory motion of the eyeball; and photophobia, an abnormal sensitivity to or intolerance of light. In one embodiment, treatment of a retinal disorder or condition is determined by improvement in any one of these symptoms.

Macular degeneration disorders include very common conditions that affect older patients (age-related macular degeneration or AMD) as well as rarer, earlier-onset dystrophies that in some cases can be detected in the first decade of life. Macular degeneration diseases include, for example, age-related macular degeneration, North Carolina macular dystrophy, Sorsby's fundus dystrophy, Stargardt's disease, pattern dystrophy, Best disease, malattia leventinese, Doyne's honeycomb choroiditis, dominant drusen and radial drusen.

Age-related macular degeneration (AMD), the most prevalent macular degeneration, is associated with progressive diminution of visual acuity in the central portion of the visual field, changes in color vision, and abnormal dark adaptation and sensitivity.

Another example of a retinal disorder that may be treated using exemplary embodiments of the methods and compositions described herein is retinitis pigmentosa or diabetic retinopathy. Retinitis pigmentosa (RP) is a collection of heritable retinal degenerations caused by defects in one of several genes for proteins of photoreceptor (PR) cells. RP is characterized by progressive rod photoreceptor degeneration and eventual blindness. The exact molecular pathogenesis of RP is still unexplained. Ultrastructural observations suggest that the rod PRs are severely affected in the disease. The clinical symptoms of retinitis pigmentosa include night blindness and loss of peripheral vision. With time visual impairment progresses toward the center of the retina causing "tunnel-vision." Retinitis pigmentosa can be subdivided into several genetic categories: autosomal dominant (adRP), autosomal recessive (arRP), X-linked (xIRP) or syndromic. There are also a number of clinical classes for retinitis pigmentosa. These classes have been condensed into two broad categories. Type 1 retinitis pigmentosa is characterized by rapid progression and diffuse, severe pigmentation; type 2 retinitis pigmentosa has a slower progression and more regional, less severe pigmentation.

FIG. 1 depicts a cross-section view 100 of an eye suitable for treatment by exemplary embodiments. FIG. 1 shows, among other things, the retina 112 and choroid 114, as well a magnified view 120 of the retina 112. The retina 112 includes the following layers: The Nerve Fiber layer 122, the Ganglion Cell layer 124, the Inner Plexiform layer 126, the Inner Nuclear layer 128, the Outer Plexiform layer 130, the Outer Nuclear layer 132, the External Limiting membrane 134, Photoreceptors 136, and Retinal Pigment Epithelium 138.

The Retinal Pigment Epithelium (RPE) 138 is the layer of pigmented cells outside of the retina that serves as a barrier between the layers of the retina 111 and the choroid 114. The RPE 138 allows small molecules, such as amino acids, to pass through it while preventing the passage of larger molecules, such as blood borne substances provided by the choroids 114. Thus, in order to get larger molecules, such as therapeutic agents, to the inner layers of the retina 112, exemplary embodiments break down or otherwise alter the RPE 138. In some exemplary embodiments, this is achieved through irradiation with a laser.

Figure 2:
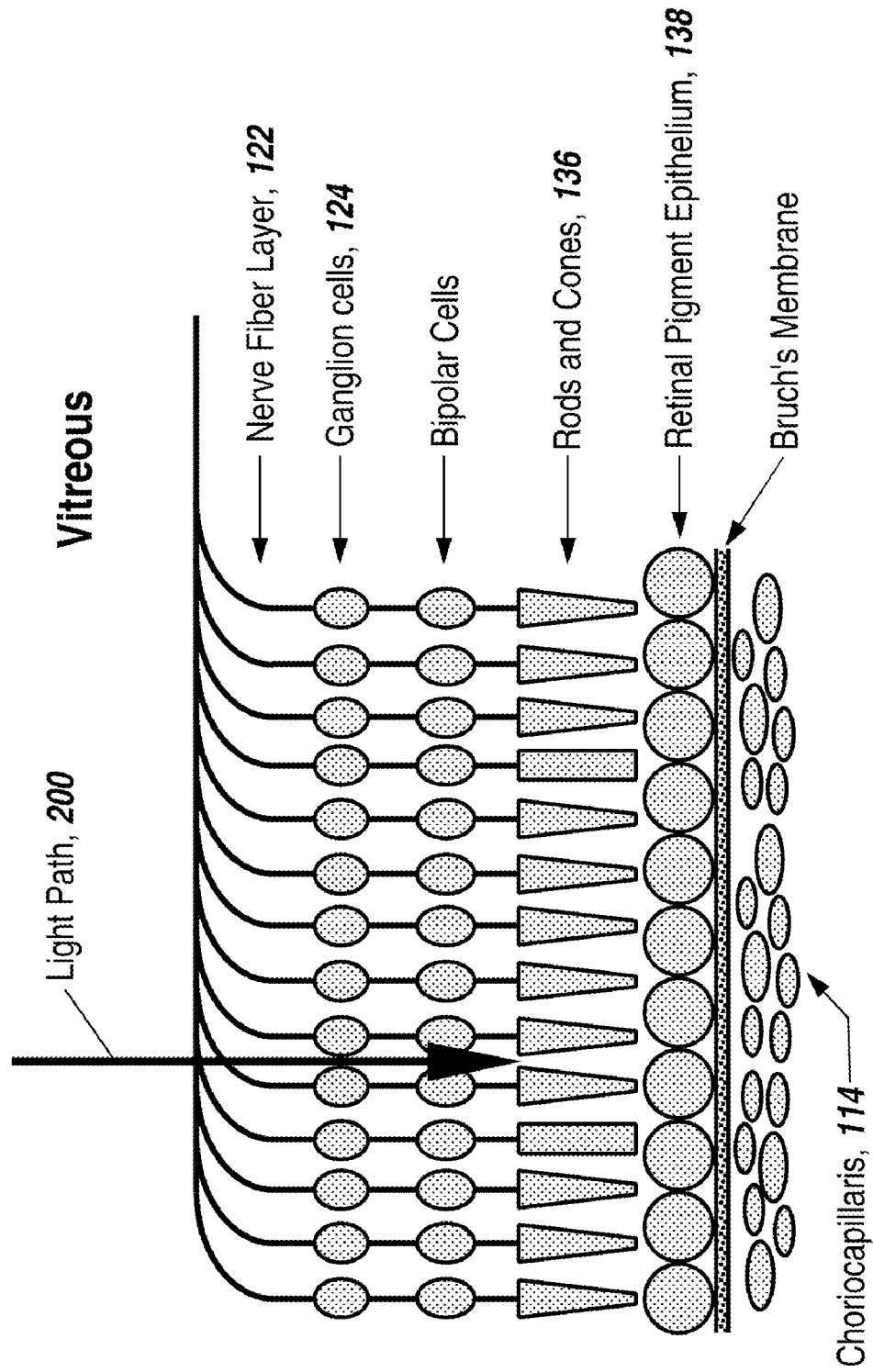
FIG. 2 is a diagrammatic illustration of an example light path of laser radiation passing into the eye.

FIG. 2 provides an example of the light path 200 of laser radiation through the layers of the retina to the RPE 138. As can be seen, the light path 200 of the laser radiation passes through the Nerve Fiber layer 122, Ganglion Cell layer 124, and Photoreceptors (rods and cones) 136 to the RPE 138.

Some exemplary embodiments use a single pulse or a series of pulses of laser radiation having low fluence such that selective targeting or alteration of the blocking tissue (such as the RPE 138) can be achieved without damage to surrounding tissues or structures. Fluences of between about 1 µJoules/cm$^2$ and about 2 Joules/cm$^2$ allow for the breakdown of the Retinal Pigment Epithelium (RPE) 138 without significantly damaging the overlying retinal layers. In one embodiment, the fluence is between about 3 µJoules/cm$^2$ and about 2 Joules/cm$^2$. The radiant exposure levels depend at least in part on the size of the area being irradiated, the duration of the pulse, the delivered joules/pulse, and the type of laser used.

The size of the area being irradiated may be between 10 µm and 5 mm. The pulses may have a duration of between about 1 nsec to 15 µsec. In one embodiment, the pulses are between about 3 ns and about 10 µsec. In certain embodiments, breakdown of the Retinal Pigment Epithelium (RPE) 138 may occur after a single pulse. In other embodiments, multiple pulses or a series of pulses, or a scanning technique may be used. The pulse duration affects the radiant exposure level as well as heat build-up at the irradiated area. Longer pulse durations increase the chance of heat build-up at the targeted area based on the thermal relaxation time of the target tissue. For the example of the RPE, the thermal relaxation time is on the order of 1-5 µsec. If the pulse duration is much longer than the thermal relaxation time of the tissue, such heat build-up can result in damage to the surrounding tissue. Thus, shorter pulse durations enable the delivery of the desired radiation while avoiding excessive heating.

There are a variety of commercially available laser systems for ophthalmic use, which may be adapted for use with exemplary embodiments. Certain modifications to the laser systems will be apparent to one skilled in the art given the benefit of this disclosure.

In accordance with one exemplary embodiment, the laser system is a Nd:YAG q-switched laser. Such lasers emit radiation at a wavelength of about 1064 nm. When the frequency is doubled such Nd:YAG lasers output at about 532 nm. Both wavelengths are useful as they are transmitted by ocular media and structures including the cornea, aqueous humor, lens, vitreous, and retina.

Figure 3:
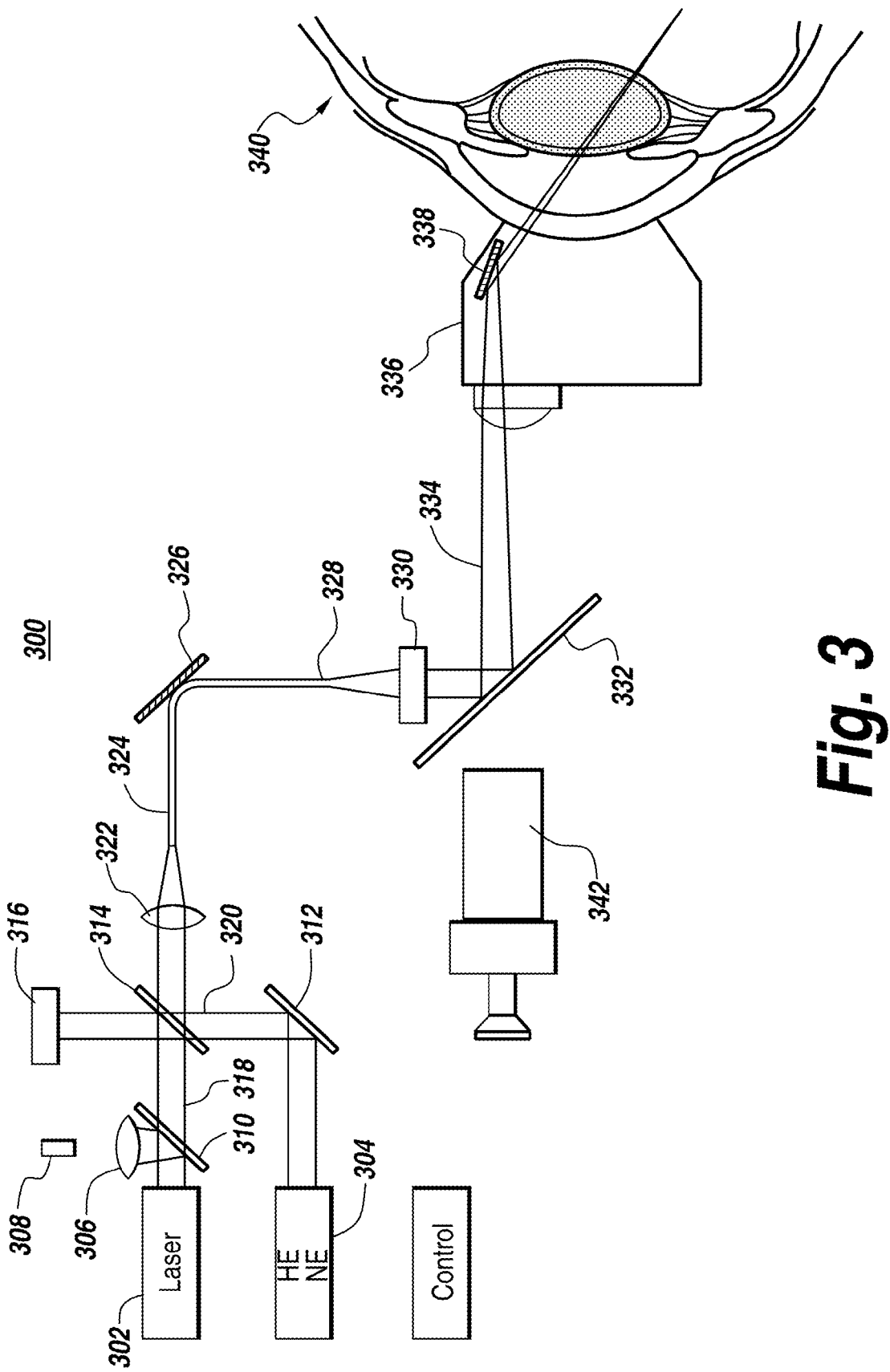
FIG. 3 is a diagrammatic illustration of an example laser system suitable for use in conjunction with the present invention.

An example of a laser system 300 appropriate for use in conjunction with exemplary embodiments is depicted in FIG. 3. As illustrated, the laser beam system consists of a power source 302 and an aiming beam source 304. The power source for the example mode of the invention is an Nd:YAG laser that is q-switched, with or without a frequency doubler, or a q-switched ruby laser, a Nd:YLF laser, a pulsed dye-laser, or a titanium sapphire laser The system may include a lens 306 and detector 308 to monitor either wavelength or power emitted by the power source 302, a component of which is deflected off of a beam splitter 310. The aiming beam source 304 emits a beam which is deflected off of a mirror 312 to another splitter 314 at which one component is deflected through the remainder of the system, while another component passes through to a beam stop 316.

A power source beam 318 and an aiming beam 320 jointly pass through a lens 322, which focuses the beams 318, 320 to pass through a 100-600 micron optical fiber 324, having another mirror 326 therein. A guided beam 328 passes through a lens 330 and then is deflected by a mirror 332. The energy 334 deflects off of the mirror 332 and into goniolens 336 where it is appropriately directed to the target tissue. After further deflecting off another mirror 338, virtually parallel beams then pass through target eye 340 to the Retinal Pigment Epithelium (RPE) 138 (not shown in this figure).

The system may also include a viewing device 32, such as a camera or view piece, for viewing the aiming light for positioning and monitoring the application of laser radiation. In accordance with one example embodiment of the present invention, laser irradiation is delivered through a slit-lamp delivery system, such that an appropriate radiant exposure is achieved at the focal point of the slit-lamp optics.

One having ordinary skill in the art will recognize that the laser system 300 depicted in FIG. 3 is exemplary, and that various modifications may be made to the laser system 300 without departing from the scope of the invention.

Energy levels can be varied using a variety of techniques. One technique utilizes a Neutral density (ND) filters for attenuating the primary Nd:YAG laser beams. In some embodiments, a variable step metallic ND filter may be used. A Helium-Neon laser is used for aiming purposes. Other possible laser systems include a scanning continuous wave laser, flashlamp-pumped dye lasers or Nd:YLF or other pulsed lasers having a 1 nsec-15 μsec pulse duration.

Once the Retinal Pigment Epithelium (RPE) 138 has been irradiated by laser energy to induce the breakdown of the RPE 138 at the selected area, a therapeutic agent may be administered such as by intravenous injection, transscleral delivery, or any other local delivery methods. The breakdown of the Retinal Pigment Epithelium (RPE) 138 allows the passage the therapeutic agent, which may be of variable size and molecular weight. After breakdown of the RPE 138, therapeutic agents having molecular weights between about 200 to 156,000 daltons may be passed to the retina and subretinal space to treat a condition.

Exemplary embodiments provide a means for temporarily altering the RPE barrier, such that therapeutic agents may be delivered, for example, into the subretinal space and retina. Therapeutic agents may also be delivered intravenously or transclerally in accordance with exemplary embodiments.

In one embodiment of the present invention, a therapeutic agent is delivered using the methods and compositions described herein for the treatment of macular degeneration. The term "macular degeneration" refers to any of a number of conditions in which the retinal macula degenerates or becomes dysfunctional, e.g., as a consequence of decreased growth of cells of the macula, increased death or rearrangement of the cells of the macula (e.g., RPE cells), loss of normal biological function, or a combination of these events. Macular degeneration results in the loss of integrity of the histoarchitecture of the cells of the normal macula and/or the loss of function of the cells of the macula. The term also encompasses extramacular changes that occur prior to, or following dysfunction and/or degeneration of the macula. Any condition which alters or damages the integrity or function of the macula (e.g., damage to the RPE or Bruch's membrane) may be considered to fall within the definition of macular degeneration. Other examples of diseases in which cellular degeneration has been implicated include retinal detachment, chorioretinal degenerations, retinal degenerations, photoreceptor degenerations, RPE degenerations, mucopolysaccharidoses, rod-cone dystrophies, cone-rod dystrophies and cone degenerations.

Figure 4B:
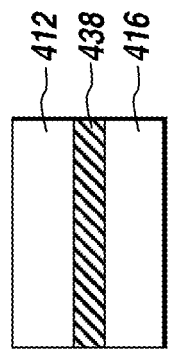

An exemplary procedure for treatment of a target tissue is depicted in FIGS. 4a-4d. As depicted in FIG. 4b, a target region of tissue 400 includes a target tissue 412, a blockage layer 438, and surrounding tissue 416. At step 410 in FIG. 4a, prior to breaking down the blockage layer 438, effective delivery of therapeutic agents is prohibited by the blockage layer 438. The target tissue 412 may correspond, for example, to the inner layers of the retina 112 depicted in FIG. 1. The blockage layer 438 may be, for example, the Retinal Pigment Epithelium 138.

With reference to FIG. 4b, a target region of tissue 400 includes a target tissue 412, a blockage layer 438, and surrounding tissue 416. At step 410 in FIG. 4a, prior to breaking down the blockage layer 438, effective delivery of therapeutic agents is prohibited by the blockage layer 438.

Figure 4C:
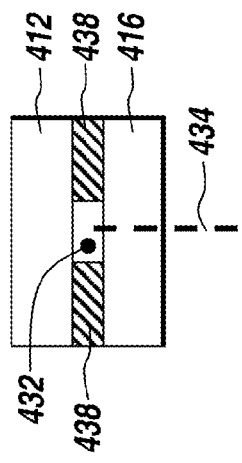
Figure 4D:
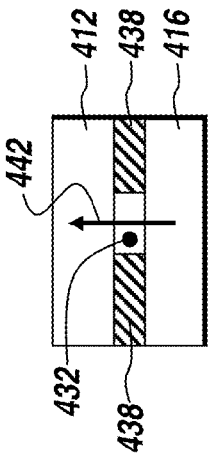
Figure 4A:
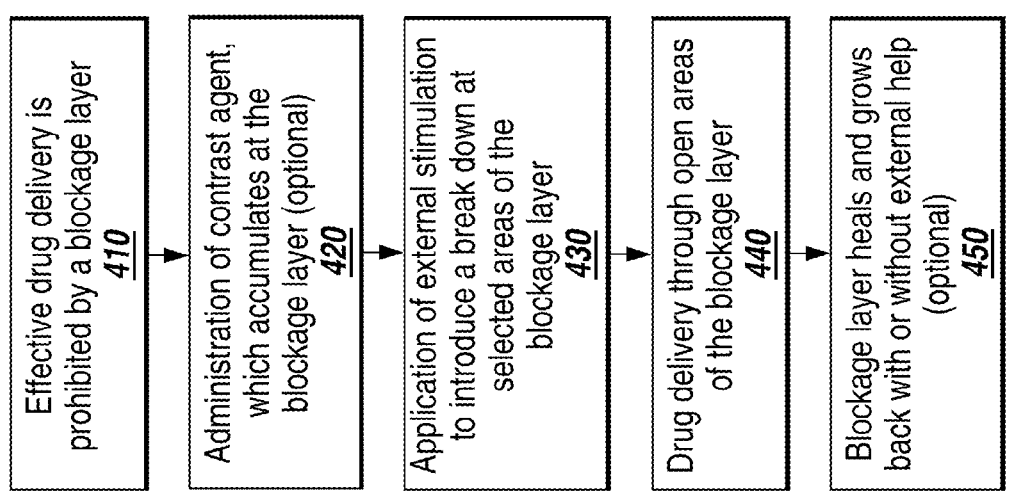
FIG. 4a is a flowchart of steps performed in an exemplary method according to the present invention.

Optionally, at step 420 in FIG. 4a, a contrast agent or photosensitizing agent may be administered to the target tissue region 400. The contrast agent may accumulate at the blockage layer 438. Exemplary contrast agents may be, or may be similar to, the contrast agents used in Photodynamic Therapy (PDT).

At step 430, external stimulation 434 is applied to blockage layer 438. This may result in an opened area 432 in the blockage layer 438, as depicted in FIG. 4c. External stimulation 434 may include stimulation by a laser, as described above. The resulting opened area 432 may be an area in the blockage layer with improved permeability as compared to blockage layer 438. For example, in FIG. 1, to induce breakdown of the Retinal Pigment Epithelium (RPE) 138, an area of the RPE 138 is targeted with a laser. The laser radiation passes through the patient's eye and the layers of the retina to induce breakdown of the RPE 138.

In accordance with exemplary embodiments of the present invention, at step 440 of FIG. 4a and in FIG. 4d, a therapeutic agent may be delivered 442 through the open area 432 of the blockage layer 438. For example, the methods and/or compositions of the invention may be used to treat a retinal disorder by delivering a therapeutic agent(s) to a patient in need thereof. The therapeutic agent may, for example, be delivered to the subretinal space and/or overlying retina of a patient.

Examples of suitable therapeutic agents that may be delivered to a patient using the methods described herein for the treatment of a retinal disorder include, but are not limited to, pegaptanib sodium, bevacizumab, VEGF Trap (Regeneron), and ranibizumab. Other therapeutic agents may take the form of prodrugs or nanoparticles. In one example embodiment, the therapeutic agent is a viral vector for use in gene eye therapy to deliver a gene to restore vision, such as, but not limited to, RPE65. Thus, the invention may be used in combination with gene therapy to treat a hereditary eye disease, such as Leber congenital amaurosis.

In certain embodiments, the therapeutic agent may be delivered intravenously. In other embodiments, the therapeutic agent may be introduced into the subtenon's space or surrounding orbital tissue or delivered transsclerally or by iontophoresis. In some exemplary embodiments, the delivery coincides with the laser induced breakdown of the Retinal Pigment Epithelium (RPE) 138. Such breakdown can occur within about 1 to 96 hours post irradiation.

In accordance with some example embodiments of the present invention, the therapeutic agent may be inactive while in the blood stream but be active when it enters the retina or subretinal space. For example, a prodrug may have an inactive form useful for absorption, distribution, and metabolism, and an active form useful for treatment. The prodrug may be administered in the inactive form, or in a form that is substantially less active than the active form. The prodrug may be activated once it has been delivered to the target tissue (for example, once the prodrug has been delivered to the eye). In some such embodiments, the therapeutic agent may be activated by a laser having a different wavelength or power level resulting in a specific photochemical reaction allowing activation. In other such embodiments, the inactive therapeutic agent may be cleaved or otherwise activated by local enzymes or activated by light.

The induced breakdown of the blockage layer 438 may be temporary. In some embodiments, as depicted at step 450 of FIG. 4a, the blockage layer 438 may heal and grow back without external assistance. In the examples described above, the breakdown of the Retinal Pigment Epithelium (RPE) 138 is not permanent. After breakdown, the RPE 138 will repair itself within, for example, days, thereby restoring normal function of the RPE 138.

Alternatively, external assistance may be provided to heal or re-grow the blockage layer. In one embodiment, medicine is administered, either directly onto the blockage layer or intravenously. In another embodiment, stem cells are applied to the blockage layer. Stem cells are cells with the ability to renew themselves through mitotic cell division and differentiate into a diverse range of specialized cell types. Stem cells may be applied to the blockage layer to replace or promote the regeneration of cells that were broken down due to the external stimulation 434, or to promote treatment of the retinal disorder.

In practice, the procedure involves anesthetizing the patient with proparicaine topical ocular anesthesia. A retinal laser lens is then placed on the patient's eye and the eye is treated in various regions through a dilated pupil. A laser system as described above is used to provide pulsed laser irradiation such that the resulting laser lesions are not visible opthalmoloscopically. That is, there is no visible whitening or change in the overlying neural retina.

Treatment effects can be confirmed by subsequent fluorescein angiography, which allow visual treatment of the retina. Following treatment, usually within about 1-6 hours, the therapeutic agent may be administered either intravenously or via transscleral delivery. Healing of the Retinal Pigment Epithelium (RPE) can be confirmed by repeat angiography.

In one embodiment of the present invention, the above-described method may be used to treat macular edema, a condition in which fluid and protein deposits collect on or under the macula of the eye, causing the macula to thicken and/or swell. The RPE may be selectively treated in accordance with the present invention, and a treatment may be administered. The treatment may be, for example, an intravenously-administered steroid or a drug which improves RPE pump function (including, but not limited to, acetazolamide).

In another embodiment of the present invention, the above-described method may be used to treat glaucoma, a disease of the optic nerve in which high intraocular pressure results in a loss of retinal ganglion cells. In this embodiment, the RPE is treated with the laser adjacent to the optic nerve, which allows for the administration of neurtrophic factors or anti-glaucoma medications to the region surrounding the optic nerve. This treatment may promote the survival of the optic nerve and the ganglion cells of the retina.

Those skilled in the art will recognize, or be able to ascertain using no more than routine experimentation, many equivalents to the specific embodiments of the invention described herein. Such equivalents are intended to be encompassed by the following claims. This invention is further illustrated by the following example which should not be construed as limiting. The contents of all references, patents and published patent applications cited throughout this application are incorporated herein by reference.

EXAMPLE

Example 1

Selective Targeting of the Retinal Pigment Epithelium (RPE) Using Laser Irradiation The following example describes a study which examined selective targeting of the RPE using laser irradiation in an animal model. The targeting of the RPE was monitored by optical coherence tomography (OCT) and fluorescein angiography.

Methods and Materials

The laser was set up according to the following parameters. A pulsed dye laser was set at 590 nm; the FWHM of the laser pulse was 1 μsec. The laser was delivered through a 1 mm diameter, 2 m long optical fiber (0.22 NA) to a beam steerer, which sits on a conventional slit lamp. The lens system inside the beam steerer ensures that the lasing spot has a hat top profile.

The energy of the laser delivered to the animal was controlled by a stepped variable metallic ND filter wheel with 8 attenuation steps at 0.04, 0.1, 0.2, 0.3, 0.4, 0.5, 0.6, and 1.0 OD respectively. The pulse energy was measured using an energy power meter. The lasing procedure was monitored using the slit lamp and also a digital CCD camera. Table 1 describes the lasing energy for the dye laser, and Table 2 describes the lasing energy for the Nd:YAg laser. The threshold for the lasing energy for the pulsed-dye laser was determined to be between ND filters 3 and 4 (about 70 mJ/cm$^2$), while the threshold for the Nd:Yag laser was determined to be between energy levels 8-50 mJ/cm$^2$.

TABLE 1

| Lasing energy for the dye laser (1 μsec pulse) | | | |
|---|---|---|---|
| ND filter | OD | Energy (mJ) | Fluence (mJ/cm$^2$) |
| 1 | 0.04 | 1.1 | 140.1273885 |
| 2 | 0.1 | 0.960234208 | 122.322829 |
| 3 | 0.2 | 0.821487619 | 104.6481044 |
| 4 | 0.3 | 0.622268355 | 79.26985409 |
| 5 | 0.4 | 0.474476835 | 60.44290895 |
| 6 | 0.5 | 0.337722001 | 43.02191094 |
| 7 | 0.6 | 0.284079945 | 36.188528 |
| 8 | 1 | 0.146947374 | 18.71941068 |

TABLE 2

Lasing energy needed for the Nd:Yag laser

| Energy (µJ) | Fluence (mJ/cm²) |
|---|---|
| 180 | 143.2 |
| 140 | 111.4 |
| 120 | 95.49 |
| 100 | 79.58 |
| 90 | 71.62 |
| 80 | 63.66 |
| 70 | 55.7 |
| 60 | 47.75 |
| 50 | 39.79 |
| 40 | 31.83 |
| 30 | 23.87 |
| 20 | 15.92 |
| 10 | 7.958 |

Dutch Belted rabbits were used as the animal model for the experiments. The rabbit retina has a more uniform pigmentation than other animal models and more closely resembles the pigmentation in the human retina. The rabbit eye also closely approximates the human eye.

The procedure included first allowing the laser system to warm up and calibrating the laser according to standard methods. The rabbit was prepared by dilating its pupils and delivering anesthesia. The rabbit was then positioned into the laser slit-lamp delivery system. Lasing was performed at different parameters. Following the lasing, the rabbit was given ophthalmoscopic evaluation, as well as OCT and FA eye examinations at various time intervals, ranging from 1 hour to about 1 month following lasing. The retinas were then evaluated using histology.

For the dye laser, 590 nm, 1 µsec pulse duration, 1 mm spot size, at the dosage of about 50 to 100 mJ/cm², the OCT results suggest that selective targeting of RPE was achieved using single laser pulse. The lesions were ophthalmoscopically invisible below 70 mJ/cm² pulse energy with a 1 µsec pulse; the OCT results showed that the retina layer was intact, while the fluorescein angiography demonstrated clear leakage at the lasing spots. For the Nd:Yag laser, 532 nm, 3-ns pulse duration, 400 µm spot size, at the dosage of about 8 to 50 mJ/cm², the OCT results suggested that selective targeting of RPE was achieved using a single laser pulse. The lesions were ophthalmoscopically invisible, the OCT and histology results showed that the retina layer was intact, while the fluorescein angiography demonstrated clear leakage at the lasing spots. Histological examination of the rabbit retina also confirms selective treatment of the RPE without thermal damage to the overlying retina.

A second experiment was performed using six Dutch Belted rabbits to selectively deliver drugs with high molecular weight into the retinal and subretinal space using selective pulsed laser treatment of the Retinal Pigment Epithelium (RPE). The rabbits were irradiated with a pulsed dye laser (Palomar 3010; 590 nm, 1 µs, 1 mm dia) and a Q-switched Nd:Yag laser (Selecta II, Lumenis; 532 nm, 3 ns, 400 µm dia). Dose studies were conducted to determine the threshold laser energies for selective RPE targeting. Further, drug delivery studies were conducted using intravenous delivery of fluorescein isothiocyanate labeled dextrans (FITC-dextran) with 10K and 40K molecular weight. Following the treatment, ophthalmoscopic examination, Fluoresein Angiography, Optical Coherence Tomography (Spectralis, Heidelberg Engineering) and histology (1 um sections) were performed on the rabbits. The rabbits were examined immediately and up to 5 weeks post treatment.

The experiment showed that selective targeting of RPE can be achieved at about 0.5 mJ (64 mJ/cm²) for the dye laser and 10 µJ (8 mJ/cm²) for the Nd:Yag laser, where the lesion is ophthalmoscopically invisible and angiographically visible. After administration of FITC-dextran with 10K molecular weight, angiography showed positive leakage within 2 minutes post-injection. For 40K Dextran, positive leakage was achieved within 40 minutes. In both cases, leakage was localized to the treatment areas. The RPE barrier was re-established within two weeks as demonstrated by negative leakage using routine fluorescein angiography. Histology at 2 days post-treatment showed that the disruption of the RPE was localized to the treated areas. The disruption was greater with the Nd:YAG than the dye laser, without gross damage to the neural retina. By 5 weeks post treatment, mild RPE pigment clumping was found only at the treated areas. The overlying layers, including the photo receptor layer, were intact.

These results indicate that large molecular weight substances can be effectively delivered across the RPE barrier following selective treatment of the RPE, while preserving the overlying neural retina. The RPE barrier is re-established later. This allows for the selective delivery of large molecular weight drugs across the RPE barrier into the retinal and subretinal space, which may be useful for the treatment of retinal diseases.

Laser irradiation of the retina can also be performed using sub-threshold repetitively pulsed lasers using a technique called high repetition rate photocolagulation (Roider, Hillenkamp, Flotte, Birngruber. *Microphotocoagulation: Selective Effects of Repetitive Short Laser Pulses*, Proc. Natl. Acad. Sci, Vol 90, pp. 8643-8647, September 1993).

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure and method may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention that, as a matter of language, might be said to fall therebetween.

What is claimed is:

1. A method of delivering a therapeutic agent to a retina of a patient, the method comprising:
    irradiating an area of a retinal pigment epithelium of a patient's eye with laser radiation in such a way that induces a breakdown or an alteration of the area in an amount sufficient to create an open area sufficient to enable the therapeutic agent to pass therethrough, the laser radiation having a fluence between about 3 µJoules/cm² and about 2 Joules/cm²; and
    administering the therapeutic agent to the patient after or during the step of irradiating the area of the retinal pigment epithelium, such that the therapeutic agent passes through the open area created by the laser radiation and is thereby delivered to the retina.

2. The method of claim 1, wherein the therapeutic agent is administered intravenously or by local application/injection or iontophoresis.

3. The method of claim 1, wherein administration of the therapeutic agent is achieved by one of the group of transscleral delivery, introduction of the therapeutic agent into the subtenon's space, and introduction of the therapeutic agent through a surrounding orbital tissue.

4. The method of claim 1, wherein the therapeutic agent is activated by irradiating the therapeutic agent with laser radiation.

5. The method of claim 1, wherein the area is irradiated using one or more laser pulses or a series of pulses having a duration of between about 1 ns and about 15 µs.

6. The method of claim 1, wherein the laser radiation is provided by one of a q-switched Nd:YAG laser, a Pulsed-Dye laser, and a Nd:YLF laser.

7. The method of claim 1, wherein the laser radiation is provided by a q-switched Nd:YAG laser.

8. The method of claim 1, wherein the laser radiation is provided by a continuous wave laser in which the laser energy is delivered via a scanning device.

9. The method of claim 1, wherein the laser radiation is provided by a flashlamp-pumped dye laser.

10. The method of claim 1, wherein the therapeutic agent administered has a molecular weight between about 200 and 156000 daltons.

11. The method of claim 1, further comprising administering a contrast agent.

12. A method of treating a retinal disorder in a patient, said method comprising:
irradiating an area of a retinal pigment epithelium of a patient's eye with laser radiation in such a way that induces a breakdown or an alteration of the area in an amount sufficient to create an open area sufficient to enable the therapeutic agent to pass therethrough, the laser radiation having a fluence between about 3 µJoules/cm$^2$ and about 2 Joules/cm$^2$; and
administering the therapeutic agent to the patient after or during the step of irradiating the area of the retinal pigment epithelium, such that the therapeutic agent passes through the open area created by the laser radiation, thereby treating the retinal disorder.

13. The method of claim 12, wherein the retinal disorder is selected from the group consisting of macular degeneration, retinitis pigmentosa and diabetic retinopathy.

14. The method of claim 12, wherein the therapeutic agent is selected from the group consisting of pegaptanib sodium, bevacizumab, VEGF Trap, and ranibizumab.

15. A method of treatment, the method comprising:
irradiating a blocking tissue area with laser radiation in such a way that induces a breakdown or an alteration of the blocking tissue area in an amount sufficient to create an open area sufficient to enable the therapeutic agent to pass therethrough, the laser radiation having a fluence of between about 1 µJoules/cm$^2$ and about 2 Joules/cm$^2$; and
administering the therapeutic agent to the target tissue through the open area created by the laser radiation after or during the step of irradiating the area of the retinal pigment epithelium.

16. The method of claim 15, further comprising administering stem cells to the block tissue area to promote the healing of the blocking tissue area.

17. The method of claim 1, wherein the step of administering the therapeutic agent to the patient occurs after the step of irradiating the area of the retinal pigment epithelium.

18. The method of claim 12, wherein the step of administering the therapeutic agent to the patient occurs after the step of irradiating the area of the retinal pigment epithelium.

19. The method of claim 15, wherein the step of administering the therapeutic agent to the target tissue occurs after the step of irradiating the blocking tissue area.

* * * * *